United States Patent [19]
Downs et al.

[11] Patent Number: 5,954,683
[45] Date of Patent: Sep. 21, 1999

[54] COMPOSITION AND COATING FOR A DISPOSABLE TAMPON APPLICATOR AND METHOD OF INCREASING APPLICATOR FLEXIBILITY

[75] Inventors: Suzanne E. Downs, Ho-Ho-Kus, N.J.; Robert Jay Axelrod, Orefield, Pa.

[73] Assignee: Playtex Products, Inc., Westport, Conn.

[21] Appl. No.: 08/632,201

[22] Filed: Apr. 15, 1996

[51] Int. Cl.$^6$ ........................................ A61F 13/20
[52] U.S. Cl. .............................................. 604/15
[58] Field of Search ........................... 604/11–18

[56] References Cited

U.S. PATENT DOCUMENTS

| | | |
|---|---|---|
| 1,926,900 | 9/1933 | Haas . |
| 2,509,241 | 5/1950 | Mende . |
| 3,419,005 | 12/1968 | Lewing . |
| 3,717,149 | 2/1973 | Morane . |
| 3,724,462 | 4/1973 | Hanke . |
| 3,760,808 | 9/1973 | Bleuer . |
| 3,796,219 | 3/1974 | Hanke . |
| 3,882,196 | 5/1975 | Hanke . |
| 3,882,869 | 5/1975 | Hanke . |
| 3,911,917 | 10/1975 | Hanke . |
| 3,954,104 | 5/1976 | Kraskin et al. . |
| 4,077,408 | 3/1978 | Murray et al. . |
| 4,077,409 | 3/1978 | Murray et al. . |
| 4,088,132 | 5/1978 | Wood et al. . |
| 4,099,976 | 7/1978 | Kraskin et al. . |
| 4,140,668 | 2/1979 | Sumi et al. . |
| 4,251,643 | 2/1981 | Harada et al. . |
| 4,309,510 | 1/1982 | Kleber . |
| 4,317,447 | 3/1982 | Williams . |
| 4,323,492 | 4/1982 | Zimmermann et al. . |
| 4,372,311 | 2/1983 | Potts . |
| 4,389,506 | 6/1983 | Hassall, Jr. . |
| 4,412,833 | 11/1983 | Wiegner et al. . |
| 4,454,194 | 6/1984 | Luebbe, Jr. . |
| 4,469,837 | 9/1984 | Cattaneo . |
| 4,478,971 | 10/1984 | Ballard . |
| 4,479,997 | 10/1984 | Masterton et al. . |
| 4,482,599 | 11/1984 | Luebbe, Jr. et al. . |
| 4,488,158 | 12/1984 | Wirnowski . |
| 4,508,531 | 4/1985 | Whitehead . |
| 4,522,967 | 6/1985 | Sheldon et al. . |
| 4,536,532 | 8/1985 | Miller et al. . |
| 4,542,178 | 9/1985 | Zimmermann et al. . |
| 4,543,086 | 9/1985 | Johnson . |
| 4,547,329 | 10/1985 | Dombroski et al. . |
| 4,611,019 | 9/1986 | Lutzmann et al. . |
| 4,650,459 | 3/1987 | Sheldon . |
| 4,656,216 | 4/1987 | Muller et al. . |
| 4,692,494 | 9/1987 | Sonenstein . |
| 4,792,326 | 12/1988 | Tews . |
| 4,849,256 | 7/1989 | Newman et al. . |
| 4,900,299 | 2/1990 | Webb . |
| 4,923,440 | 5/1990 | Genaro . |
| 4,950,513 | 8/1990 | Mehra . |
| 5,002,526 | 3/1991 | Herring . |
| 5,015,501 | 5/1991 | Johnson . |
| 5,028,648 | 7/1991 | Famili et al. . |
| 5,070,126 | 12/1991 | Toyonishi et al. . |
| 5,093,401 | 3/1992 | Claussen et al. . |
| 5,135,475 | 8/1992 | Nakanishi et al. . |
| 5,137,969 | 8/1992 | Marten et al. . |
| 5,158,535 | 10/1992 | Paul et al. . |
| 5,187,226 | 2/1993 | Kamachi et al. . |
| 5,190,712 | 3/1993 | Oishi et al. . |
| 5,258,430 | 11/1993 | Bastioli et al. . |
| 5,262,458 | 11/1993 | Bastioli et al. . |
| 5,279,541 | 1/1994 | Frayman et al. . |
| 5,290,501 | 3/1994 | Klesius . |
| 5,330,421 | 7/1994 | Tarr et al. . |
| 5,346,468 | 9/1994 | Campion et al. . |
| 5,348,534 | 9/1994 | Tomaszewski et al. . |
| 5,349,000 | 9/1994 | Robeson et al. . |
| 5,350,354 | 9/1994 | Billmers . |
| 5,360,830 | 11/1994 | Bastioli et al. . |
| 5,380,529 | 1/1995 | Heusser et al. . |
| 5,389,068 | 2/1995 | Keck . |
| 5,395,308 | 3/1995 | Fox et al. . |
| 5,494,709 | 2/1996 | Long, Jr. et al. . |

FOREIGN PATENT DOCUMENTS

| | | |
|---|---|---|
| 260512 | 5/1963 | Australia . |
| 281145 | 4/1965 | Australia . |
| 860911 | 1/1971 | Canada . |
| 2053219 | 10/1991 | Canada . |
| 0 291 024 | 11/1988 | European Pat. Off. . |
| 0 551 758-A1 | 7/1993 | European Pat. Off. . |
| 0 585 906-A2 | 3/1994 | European Pat. Off. . |

*Primary Examiner*—John G. Weiss
*Assistant Examiner*—Dennis Ruhl
*Attorney, Agent, or Firm*—Ohlandt, Greeley, Ruggiero & Perle

[57] ABSTRACT

There is provided a water dissolvable tampon applicator comprising a first polyvinyl alcohol, a second polyvinyl alcohol having a lower percent hydrolysis than said first polyvinyl alcohol, a plasticizer. Preferably, the first polyvinyl alcohol is polyvinyl alcohol 98% hydrolyzed ultra low viscosity, the second polyvinyl alcohol is polyvinyl alcohol 88% hydrolyzed ultra low viscosity, and the third polyvinyl alcohol is polyvinyl alcohol 88% hydrolyzed low viscosity. The applicator also includes a plasticizer and an antioxidant. The applicator further includes a water insoluble coating that holds moisture. The water insoluble coating is preferably a vinylidene chloride copolymer, and can be used on any polyvinyl alcohol tampon applicator. In another preferred embodiment, the applicator is exposed to humidity prior to application of the coating.

26 Claims, No Drawings

COMPOSITION AND COATING FOR A DISPOSABLE TAMPON APPLICATOR AND METHOD OF INCREASING APPLICATOR FLEXIBILITY

BACKGROUND OF THE INVENTION

I. Field of the Invention

The present invention relates generally to tampon applicators. More particularly, the present invention relates to a plastic-type tampon applicator that is biodegradable. The present invention further relates to a plastic-type tampon applicator that remains stable prior to and throughout use. By the unique treatment provided herein, all plastic-type applicators has prolonged flexibility and stable aging. In addition, the present invention includes an outer coating that retains moisture in the applicator and prevents undesirable stickiness.

Typically, tampon applicators, after use, are disposed in toilets, trash receptacles and the like. To prevent unwanted problems in septic systems and waste disposal facilities, tampon applicators must be biodegradable.

Generally, tampon applicators are made from a paper-based or plastic-based material. Certain users prefer plastic-type applicators. Such plastic-type tampon applicators are made typically of a polyethylene that is injection molded or extruded. However, polyethylene is not biodegradable. Other tampon applicators have been made of polyvinyl alcohol, which is water dispersible and biodegradable, however such applicators have been found to be sticky and not stable for long periods of time.

II. Description of the Prior Art

Tampon applicators made from polyvinyl alcohol are shown in U.S. Pat. No. 3,717,149 to Morane, which issued on Feb. 20, 1973; U.S. Pat. No. 3,724,462 to D. E. Hanke, which issued on Apr. 3, 1973; U.S. Pat. No. 3,882,196 to D. E. Hanke, which issued on May 6, 1975; and U.S. Pat. No. 3,911,917 to D. E. Hanke, which issued Oct. 14, 1975. Typically, polyvinyl alcohol is made from higher molecular weight polymers and plasticized with glycerine. Such polyvinyl alcohol, however, has been found to have poor solubility in cold water. The other type of polyvinyl alcohol, known as cold water soluble, is made from internally plasticized and lower molecular weight resins.

A polyvinyl alcohol tampon applicator that claims to be biodegradable and water dispersible is described in U.S. Pat. No. 5,002,526 to L. E. Herring, which issued on Mar. 26, 1991. The tampon applicator is made from a polyvinyl alcohol having less than about 5 percent by weight of plasticizer. This patent states that the use of plasticizers at about 20 percent by weight can be expected to result in increased moisture sensitivity, decreased tensile strength, and migration of the plasticizer from the finished product. Accordingly, this applicator produces a slimy or slippery outer surface, even before contact with water.

Other tampon applicators are made of polyvinyl alcohol with various additives, such as plasticizers and antioxidants. For example, U.S. Pat. No. 4,849,256 to G. F. Newman, which issued on Jul. 18, 1989, provides a method for producing a resin blend including a polyvinyl alcohol (PVA) resin granules that are coated with a plasticizer and then mixed with a powder coating. Other components, such as antioxidants, dyes, and antiblocking agents, may also be incorporated into the finished product. Also, U.S. Pat. No. 5,380,529 to J. Heusser, et al., which issued on Jan. 10, 1995, provides a pharmaceutical preparation for application to a vagina having a polyvinyl alcohol and at least two additional components. One component is selected from the group consisting of wetting agents, non-ionic surface active agents and dispersing agents.

Other examples of compositions that include polyvinyl alcohols with various additives are described in U.S. Pat. No. 5,190,712 to T. Oishi, et al., which issued on Mar. 2, 1993; U.S. Pat. No. 4,140,668 to Sumi, et al., which issued in 1979; U.S. Pat. No. 4,309,510 to R. Kleber, which issued on Jan. 5, 1982; U.S. Pat. No. 4,323,492 to W. Zimmermann, et al., which issued on Apr. 6, 1982; U.S. Pat. No. 4,389,506 to T. Hassall, Jr., which issued on Jun. 21, 1983; U.S. Pat. No. 4,454,194 to R. H. Luebbe, Jr., which issued on Jun. 12, 1984; U.S. Pat. No. 4,469,837 to P. Cattaneo, which issued on Sep. 4, 1984; U.S. Pat. No. 4,478,971 to L. Ballard, which issued on Oct. 23, 1984; U.S. Pat. No. 4,479,997 to Masterson, et al., which issued in 1984; U.S. Pat. No. 4,482,599 to Luebbe, Jr., et al., which issued in 1984; U.S. Pat. No. 4,488,158 to Wirnowski, which issued in 1984; U.S. Pat. No. 4,536,532 to G. W. Miller, et al, which issued on Aug. 20, 1985; U.S. Pat. No. 4,542,178 to W. Zimmermann, et al., which issued on Sep. 17, 1985; U.S. Pat. No. 4,547,329 to J. R. Dombroski, et al., which issued on Oct. 15, 1985; U.S. Pat. No. 4,611,019 to H. H. Lutzmann, et al., which issued on Sep. 9, 1986; U.S. Pat. No. 4,656,216 to A. Müller, et al., which issued on Apr. 7, 1987; U.S. Pat. No. 4,692,494 to G. G. Sonenstein, which issued on Sep. 8, 1987; U.S. Pat. No. 4,849,256 to G. F. Newman, et al., which issued on Jul. 18, 1989; U.S. Pat. No. 4,950,513 to V. K. Mehra, which issued on Aug. 21, 1990; U.S. Pat. No. 5,028,648; U.S. Pat. No. 5,070,126 to S. Toyonishi, et al., which issued on Dec. 3, 1991; U.S. Pat. No. 5,093,401 to U. Claussen, et al., which issued on Mar. 3, 1992; U.S. Pat. No. 5,137,969 to F. L. Marten, et al., which issued on Aug. 11, 1992; U.S. Pat. No. 5,187,226 to M. Kamachi, et al., which issued on Feb. 16, 1993; U.S. Pat. No. 5,190,712 to T. Oishi, et al., which issued on Mar. 2, 1993; U.S. Pat. No. 5,258,430 to C. Bastioli, et al., which issued on Nov. 2, 1993; U.S. Pat. No. 5,262,458 to C. Bastioli, et al., which issued on Nov. 16, 1993; U.S. Pat. No. 5,349,000 to Robeson, et al., which issued in 1994; U.S. Pat. No. 5,360,830 to C. Bastioli, et al., which issued on Nov. 1, 1994; and U.S. Pat. No. 5,380,529 to J. Heusser, et al., which issued on Jan. 10, 1995.

For use, the outer surface of a plastic-based tampon applicator should not be sticky, slippery or slimy. The outer surface of a tampon applicator has been coated with a water-insoluble polymer in an attempt to prevent such stickiness or slipperiness. For example, U.S. Pat. No. 4,372,311 to J. E. Potts, which issued on Feb. 8, 1983, provides a disposable article made from a water-soluble polymer in which the surface of the article is coated with a degradable water-insoluble polymer. The patent states that the degradable water-insoluble polymer can be a cyclic ester polymer, a poly (β-hydroxy butyrate), dialkanoyl polymers, such as polyesters and polyurethanes derived from aliphatic polyols, and ethylene polymers.

Thus, there still is a need for a plastic-type tampon applicator that is sufficiently moisture resistant to provide a dry, outer surface before and during use and, yet, water-dispersible for disposal into a toilet bowl after use. Moreover, there is still a need for such a plastic-based tampon applicator that remains flexible and stable for a long period of time.

SUMMARY OF THE INVENTION

Against the foregoing background, it is a primary object of the present invention to provide a water dissolvable or biodegradable tampon applicator comprising polyvinyl alcohol, a plasticizer and an antioxidant that maintains the stability of the water dissolvable applicator.

It is another object of the present invention to provide such a water dissolvable tampon applicator that has been exposed to a humidity environment after its formation, to enhance the flexibility and stable aging of the applicator.

It is still another object of the present invention to provide such a water dissolvable tampon applicator that has a water resistant or water insoluble coating that prevents stickiness.

It is a further object of the present invention to provide such a water dissolvable tampon applicator that has a water resistant or water insoluble coating that holds moisture in the applicator structure in order to prevent stickiness.

It is a still further object of the present invention to provide such a water dissolvable tampon applicator in which the water resistant or water insoluble coating is a vinylidene chloride copolymer that, after curing, provides miscible water solubility characteristics.

To accomplish the foregoing objects and advantages, the present invention, in brief summary, is a composition for a water dissolvable tampon applicator that comprises a first polyvinyl alcohol, a second polyvinyl alcohol having a lower percent hydrolysis than the first polyvinyl alcohol, and, preferably, a third polyvinyl alcohol having a lower percent hydrolysis than the first polyvinyl alcohol and a higher viscosity than the second polyvinyl alcohol. The composition further comprises a plasticizer and an antioxidant to provide stability to the composition.

The applicator preferably has a water resistant or water insoluble coating that includes a vinylidene chloride copolymer which reduces stickiness and holds moisture without substantially affecting the water dissolvable properties of the tampon applicator. This water resistant coating may also be used on existing plastic applicators known in the art.

The applicator, prior to application of the water resistant coating, is preferably subjected to humidity that results in an increase of moisture in the applicator which, thereby, results in an increase in flexibility or stable aging. The coating, if applied, acts to maintain the moisture in the applicator and, thus, further enhance the stable aging properties of the applicator.

DETAILED DESCRIPTION OF THE PREFERRED EMBODIMENT

The present invention provides a tampon applicator composed of a new plastic compound that dissolves in water for disposal after use. The plastic compound basically comprises a base resin of polyvinyl alcohol (PVA or PVOH) formed by combining at least two different polyvinyl alcohol resins each having a different percent hydrolysis, a plasticizer and one or more antioxidants. Additives may be included to improve the quality, manufacturing and aesthetics of the plastic compound and, correspondingly, facilitate the injection molding or extruding of the plastic compound into a product, such as the tampon applicator of the present invention. Such additives include a flow promoter, a mold release, a pigment and a stabilizer.

In the preferred embodiments of the present invention, the base resin, i.e., polyvinyl alcohol, is a water-soluble thermoplastic prepared by partial or complete hydrolysis of polyvinyl acetate. The polyvinyl alcohol has an empirical formula of $(C_4H_6O_2)x.(C_2H_4O)y$. The water solubility of the polyvinyl alcohol can be regulated by controlling the hydrolysis, molecular weight and viscosity of the polyvinyl alcohol. By combining two or more different polyvinyl alcohol resins having specific hydrolysis, molecular weight and viscosity properties, the water solubility of the polyvinyl alcohol is controlled.

For a preferred embodiment, three different polyvinyl alcohol resins are combined to form a base compound that is structurally stable for formation into a tampon applicator and, also, is water-soluble.

The first polyvinyl alcohol is a polyvinyl alcohol 98% (percent) hydrolyzed ultra low viscosity ingredient that is about 1.0 to about 70.0 percent by weight of the total weight of the plastic compound. The second polyvinyl alcohol is a polyvinyl alcohol 88% hydrolyzed ultra low viscosity ingredient that is about 1.0 to about 70.0 percent by weight of the total weight of the plastic compound. The third polyvinyl alcohol is a polyvinyl alcohol 88% hydrolyzed low viscosity that is about 1.0 to about 20.0 percent by weight of the total weight of the plastic compound.

The polyvinyl alcohols resins differ in that the polyvinyl alcohol 98% hydrolyzed ultra low viscosity has a higher percent hydrolysis than both the polyvinyl alcohol 88% hydrolyzed ultra low viscosity and hydrolyzed low viscosity. Also, the percent hydrolysis of the polyvinyl alcohol 88% hydrolyzed ultra low viscosity and the polyvinyl alcohol 88% hydrolyzed low viscosity are similar, but the viscosity and molecular weight of polyvinyl alcohol 88% hydrolyzed ultra low viscosity is lower than the viscosity and molecular weight of polyvinyl alcohol 88% hydrolyzed low viscosity. The first or about 98% hydrolyzed polyvinyl alcohol has a viscosity of about 3.2 to about 4.2 cps, with a number average molecular weight of 7 to 13 thousands and a weight average molecular weight of 13 to 23 thousands. The second or about 88% hydrolyzed polyvinyl alcohol has a viscosity of about 3.0 to about 4.0 cps., and with a number average molecular weight of 7 to 13 thousands and a weight average molecular weight of 13 to 23 thousands. The third or about 88% hydrolyzed polyvinyl alcohol has a viscosity of about 5.2 to about 6.2 cps with a number average molecular weight of 15 to 27 thousands and a weight average molecular weight of 31 to 50 thousands.

As stated above, in a preferred embodiment, a plasticizer is mixed with the polyvinyl alcohol ingredients. The plasticizer increases the flexibility, workability and/or distensibility of the plastic or elastomer. For the preferred embodiment, the plasticizer is about 5.0 to about 25.0 percent by weight of the total weight of the plastic compound. In the preferred embodiment, the plasticizer is Glycerine USP 96% (having a minimum content of 96% by weight of glycerine). Glycerine USP 96% is available from Dow Chemical U.S.A.

The preferred plastic compound of the present invention also includes at least one antioxidant. One antioxidant is a phenolic derivative that provides stability to the plastic compound. The antioxidant is about 0.05 to about 1.0 percent by weight of the total weight of the plastic compound. The particular phenolic derivative used for the preferred embodiment is octadecyl 3,5-di-tert-butyl-4-hydroxyhydrocinnamate having a chemical formula of $C_{35}H_{62}O_3$. One such phenolic derivative, Irgonox 1076, is available from Ciba-Geigy Corporation.

In addition to the plasticizer and the antioxidant, a stabilizer is also used in the preferred plastic compound. A preferred stabilizer is a mixture of phosphorus trichloride and other ingredients. Such a mixture of phosphorus trichloride is available from Sandoz Chemicals under the name Sandostab P-EPQ Powder. This mixture is a phosphorus trichloride that is reacted with 1,1'-biphenyl and 2,4-bis (1,1-dimethylethyl) phenol. For the preferred embodiment, one or more such stabilizers comprise about 0.50 to about 1.0 percent by weight of the total weight of the plastic compound.

The plastic compound may also include a flow promoter. For the preferred embodiment, the flow promoter is about 0.50 to about 5.0 percent by weight of the total weight of the plastic compound. The preferred flow promoter is glycerol mono oleate (GMO) which is an unsaturated distilled glycerol ester derived from vegetable oils with at least 96% monoester content. Pationic 907, available from American Ingredients Co., is the preferred GMO.

Another additive is a pigment or colorant. For the preferred embodiment, there may be no pigment or the amount of pigment can be up to about 12.0 percent by weight of the total weight of the plastic compound. Titanium dioxide ($TiO_2$), also known as titania and rutile, is used in the preferred embodiment. Titanium dioxide is an inorganic oxide that is commercially available from many sources, including DuPont Chemicals.

A mold release agent may be included in order to facilitate the manufacture of the tampon applicator. For the preferred embodiments, the mold release agent is about 0.50 to about 5.0 percent by weight of the total weight of the plastic compound. The preferred mold release is polyethylene glycol. The preferred polyethylene glycol has a molecular weight about 500. A commercially available mold release agent is TPEG 500 available from Union Carbide Chemicals and Plastics Company Inc.

Another additive that may be included is a polyvinyl alcohol ash neutralizer, such as phosphoric acid. The weight percent of the ash neutralizer is a function of the ash content of the incoming polyvinyl alcohol and, thus, will vary.

In all preferred embodiments, the surface of the applicator is coated with a water resistant coating. The coating should possess excellent flat and creased barrier properties to water vapor, gas, grease and oil and low foam characteristics. Also, the coating should be very stable to mechanical shear, and possess good film forming properties at temperatures just above room temperature and higher.

Preferably, the coating is a vinylidene chloride copolymer latex. The particular coating of the preferred embodiment is a vinylidene chloride-butyl acrylate-acrylonitrile polymer dispersion in water. The preferred particular coating is a product known as Daran SL 143 distributed by Hampshire Chemical Corporation.

This particular coating is believed effective for all known polyvinyl alcohol tampon applicators to reduce stickiness and slipperiness of the applicator. Such known applicators, as stated above, have one polyvinyl alcohol base resin, and may include a plasticizer. It is believed that this particular coating is also effective to reduce stickiness and slipperiness when used on other polyvinyl applicators.

Infrared and dielectric drying techniques should also perform well with the coating. In addition, the coating may be formulated with wax, pigment, and other additives to improve slip, block resistance and other surface characteristics, and wetability on hard-to-wet substrates.

In all preferred embodiments, the molded article is exposed to a humidified environment prior to application of the coating. The humidity environment may be created by moisture, in the form of water vapor, applied to the applicator using conventional equipment and familiar methods. However, the humidified environment can be any environment that permits the applicator to increase moisture.

Laboratory tests have found that the water vapor should, for a three (3) gram applicator, increase the applicator's weight from about 0.16 to about 0.20 grams. Thus, the added moisture is about 5.0 to about 6.6 percent by weight of the total weight of the molded article or tampon. The added moisture makes the applicator flexible for a longer period of time thereby increasing the stable "aging" of the applicator. If greater moisture than set forth above is added, the applicator has been found to be too sticky, while less moisture than set forth above has been found not to provide the desired, extended flexibility.

The coating, which is applied after exposure of the formed applicator to the humidity environment, serves as a barrier to retain moisture, including the added moisture. This feature increases the stable aging of the applicator.

It should be understood, however, that the present invention has revealed that exposure to a humidified environment will increase the flexibility and, thus, stable aging of all types of polyvinyl applicators.

The water resistant coating of the applicator is preferably applied by a pan coating process. In this pan coating process, the molded and, preferably humidified, article is placed inside a rotating "pan" or drum. Within the pan is a spray gun that delivers the coating onto the applicator or product in the form of atomized droplets. The environment inside the drum and the spray rate is optimized so as to insure that the most uniform film coating is achieved with the smallest amount of heat being added to the humidified applicator.

Typical optimum conditions for film coating using a 90 liter capacity pan coater are: an airflow of 400 to 700 cubic feet per minute (cfm), processing air temperatures of 20 to 45 degrees centigrade (C), and a spray rate of 33 gms./min.

The most preferred embodiment of the water dissolvable tampon applicator of the present invention has the following ingredients, percent composition by weight and primary function:

| Chemical Name | Percent Weight | Function |
| --- | --- | --- |
| polyvinyl alcohol 98% hydrolyzed ultra low viscosity | 35.48 | base resin |
| polyvinyl alcohol 88% hydrolyzed ultra low viscosity | 32.24 | base resin |
| polyvinyl alcohol 88% hydrolyzed low viscosity | 8.85 | base resin |
| Glycerine | 16.55 | plasticizer |
| Glycerol Mono Oleate (GMO) | 2.61 | flow promoter |
| Titanium Dioxide | 2.18 | pigment |
| Polyethylene Glycol | 1.35 | mold release |
| Phenolic derivative ($C_{35}H_{62}O_3$) | 0.11 | antioxidant & stabilizer |
| Phosphorus Trichloride mixture | 0.22 | stabilizer |
| 85% Phosphoric Acid | 0.89 | PVOH ash neutralizer |

In addition, about 1.50 percent by weight of the total weight of the applicator of Daran SL143 is applied as the coating.

The invention having been thus described with particular reference to the preferred forms thereof, it will be obvious that various changes and modifications may be made therein without departing from the spirit and scope of the invention as defined in the appended claims.

Wherefore, we claim:

1. A water dissolvable tampon applicator comprising:
   a first polyvinyl alcohol;
   a second polyvinyl alcohol having a lower percent hydrolysis than said first polyvinyl alcohol;

a plasticizer; and an antioxidant.

2. The applicator of claim 1, further comprising a third polyvinyl alcohol having a lower percent hydrolysis than said first polyvinyl alcohol and a higher viscosity than said second polyvinyl alcohol.

3. The applicator of claim 1, further comprising a water insoluble coating that includes a vinylidene chloride copolymer, wherein said coating retains moisture in the applicator.

4. The applicator of claim 2, further comprising a water insoluble coating that includes a vinylidene chloride copolymer.

5. The applicator of claim 3, wherein said water insoluble coating is a vinylidene chloride-butyl acrylate-acrylonitrile polymer that possesses moisture barrier properties.

6. The applicator of claim 2, wherein said first polyvinyl alcohol is about 98% hydrolyzed and has a viscosity of about 3.2 to about 4.2 cps.

7. The applicator of claim 6, wherein said second polyvinyl alcohol is about 88% hydrolyzed and has a viscosity of about 3.0 to about 4.0 cps.

8. The applicator of claim 7, wherein said third polyvinyl alcohol is about 88% hydrolyzed and has a viscosity of about 5.2 to about 6.2 cps.

9. The applicator of claim 2, wherein said first polyvinyl alcohol is about 1.0 to about 70.0 percent by weight, said second polyvinyl alcohol is about 1.0 to about 70.0 percent by weight, and said third polyvinyl alcohol is about 1.0 to about 20.0 percent by weight of the total weight of the applicator.

10. The applicator of claim 1, wherein said plasticizer is about 5.0 to about 25.0 percent by weight of the total weight of the applicator.

11. The applicator of claim 10, wherein said plasticizer includes glycerine.

12. The applicator of claim 1, wherein said antioxidant is about 0.05 to about 1.0 percent by weight of the total weight of the applicator.

13. The applicator of claim 12, wherein said antioxidant includes a phenolic derivative.

14. The applicator of claim 2, further comprising a stabilizer.

15. The applicator of claim 2, further comprising a flow promoter.

16. The applicator of claim 2, further comprising a mold release agent.

17. The applicator of claim 2, further comprising an polyvinyl alcohol ash neutralizer.

18. The applicator of claim 2, further comprising at least one material selected from the group consisting of: phosphorus trichloride that is reacted with 1,1'-biphenyl and 2,4-bis (1,1-dimethylethyl) phenol, glycerol mono oleate, polyethylene glycol, phosphoric acid and titanium dioxide.

19. The applicator of claim 1, wherein the applicator is exposed to humidity after formation to add moisture to the formed applicator.

20. A water dissolvable tampon applicator comprising:

a first polyvinyl alcohol;

a second polyvinyl alcohol having a lower percent hydrolysis than said first polyvinyl alcohol;

a third polyvinyl alcohol having a lower percent hydrolysis than said first polyvinyl alcohol and a higher viscosity than said second polyvinyl alcohol;

a plasticizer; and an antioxidant to provide stability to the applicator.

21. The applicator of claim 20, further comprising a water insoluble coating that includes a vinylidene chloride copolymer.

22. The applicator of claim 21, further comprising a stabilizer.

23. The applicator of claim 22, further comprising a flow promoter, a mold release agent, and an polyvinyl alcohol ash neutralizer.

24. A water dissolvable tampon applicator comprising:

an applicator body that includes:

a first polyvinyl alcohol;

a second polyvinyl alcohol having a lower percent hydrolysis than said first polyvinyl alcohol;

a plasticizer; and an antioxidant; and a water resistant coating that includes a vinylidene chloride copolymer, wherein the coating retains moisture in the applicator.

25. The applicator of claim 1, further comprising a water insoluble coating.

26. The applicator of claim 3, wherein said applicator is exposed to humidity prior to being coated with said coating.

* * * * *